(12) United States Patent
Barral et al.

(10) Patent No.: US 12,102,397 B2
(45) Date of Patent: Oct. 1, 2024

(54) STEP-BASED SYSTEM FOR PROVIDING SURGICAL INTRAOPERATIVE CUES

(71) Applicant: Verily Life Sciences LLC, South San Francisco, CA (US)

(72) Inventors: Joëlle K. Barral, Mountain View, CA (US); Martin Habbecke, Palo Alto, CA (US); Xing Jin, San Jose, CA (US); Lin Yang, Sunnyvale, CA (US)

(73) Assignee: Verily Life Sciences LLC, Dallas, TX (US)

( * ) Notice: Subject to any disclaimer, the term of this patent is extended or adjusted under 35 U.S.C. 154(b) by 208 days.

(21) Appl. No.: 16/243,543

(22) Filed: Jan. 9, 2019

(65) Prior Publication Data
US 2019/0223961 A1    Jul. 25, 2019

Related U.S. Application Data

(60) Provisional application No. 62/619,650, filed on Jan. 19, 2018.

(51) Int. Cl.
*A61B 5/00*    (2006.01)
*A61B 34/00*    (2016.01)
(Continued)

(52) U.S. Cl.
CPC .............. *A61B 34/30* (2016.02); *A61B 34/25* (2016.02); *A61B 34/37* (2016.02); *G06N 3/08* (2013.01);
(Continued)

(58) Field of Classification Search
CPC ... A61B 34/10; A61B 34/25; A61B 2034/101; A61B 2034/108; A61B 2034/2065; A61B 2034/254
See application file for complete search history.

(56) References Cited

U.S. PATENT DOCUMENTS 7,920,162 B2    4/2011  Masini et al.
8,313,432 B2    11/2012 Chiu et al.
(Continued)

FOREIGN PATENT DOCUMENTS

WO    2017/083768 A1    5/2017

OTHER PUBLICATIONS

Combination of Convolutional and Recurrent Neural Network for Sentiment Analysis of Short Texts, Wang et al., pp. 2428-2437, Osaka, Japan, Dec. 11-17, 2016. (Year: 2016).*
(Continued)

*Primary Examiner* — Sana Sahand
(74) *Attorney, Agent, or Firm* — Christensen O'Connor Johnson Kindness PLLC (57) ABSTRACT

A system for robot-assisted surgery includes an image sensor and a display. The system further includes a controller coupled to the image sensor and the display, where the controller includes logic that when executed by the controller causes the system to perform operations. The operations may include acquiring first images of a surgical procedure with the image sensor, and analyzing the first images with the controller to identify a surgical step in the surgical procedure. The operations may further include displaying second images on the display in response to identifying the surgical step; the second images may include at least one of a diagram of human anatomy, a preoperative image, an intraoperative image, or an annotated image of one of the first images.

24 Claims, 4 Drawing Sheets

(51) Int. Cl.
*A61B 34/30* (2016.01)
*A61B 34/37* (2016.01)
*G06N 3/08* (2023.01)
*G06N 20/00* (2019.01)
*G16H 30/20* (2018.01)
*A61B 1/313* (2006.01)
*A61B 17/00* (2006.01)
*A61B 34/20* (2016.01)
*A61B 34/35* (2016.01)
*A61B 90/00* (2016.01)

(52) U.S. Cl.
CPC ............ *G06N 20/00* (2019.01); *G16H 30/20* (2018.01); *A61B 1/3132* (2013.01); *A61B 2017/00128* (2013.01); *A61B 2017/00203* (2013.01); *A61B 2034/2057* (2016.02); *A61B 2034/252* (2016.02); *A61B 2034/254* (2016.02); *A61B 2034/256* (2016.02); *A61B 2034/301* (2016.02); *A61B 2034/302* (2016.02); *A61B 34/35* (2016.02); *A61B 2090/374* (2016.02); *A61B 2090/3762* (2016.02)

(56) References Cited

U.S. PATENT DOCUMENTS

| | | | |
|---|---|---|---|
| 8,560,047 | B2 | 10/2013 | Haider et al. |
| 9,767,557 | B1* | 9/2017 | Gulsun ................ G06T 7/60 |
| 9,788,907 | B1 | 10/2017 | Alvi et al. |
| 10,467,274 | B1* | 11/2019 | Ren ................... G06V 30/194 |
| 2011/0046476 | A1 | 2/2011 | Cinquin et al. |
| 2011/0230710 | A1* | 9/2011 | Hoeg ................... A61B 90/36 600/103 |
| 2014/0039906 | A1 | 2/2014 | Wang et al. |
| 2015/0057646 | A1* | 2/2015 | Aljuri ................... A61B 1/307 606/10 |
| 2016/0270861 | A1* | 9/2016 | Guru ................... A61B 34/20 |
| 2017/0011738 | A1* | 1/2017 | Senior ................. G10L 15/063 |
| 2019/0090969 | A1* | 3/2019 | Jarc ....................... A61B 90/37 |
| 2019/0122406 | A1* | 4/2019 | Wang ................... G16H 30/40 |
| 2019/0355149 | A1* | 11/2019 | Avendi ................. G06T 7/74 |
| 2020/0170710 | A1* | 6/2020 | Rus ..................... G06K 9/00335 |

OTHER PUBLICATIONS

CNN-RNN: a large-scale hierarchical image classification framework, Guo et al., pp. 10252-10266 (Year: 2017).*
Bodenstedt et al., "Unsupervised temporal context learning using convolutional neural networks for laparoscopic workflow analysis," Journal of Artificial Intelligence in Medicine, Feb. 2017, 10 pages.
Funke et al., "Temporal coherence-based self-supervised learning for laparoscopic workflow analysis," 8 pages.
Vaswani et al., "Attention Is All You Need," 31st Conference on Neural Information Processing Systems (NIPS 2017), 15 pages.
Zoph et al., "Learning Transferable Architectures for Scalable Image Recognition," 14 pages.
Endoscopic Vision Challenge 2017, "Surgical Workflow Analysis in the SensorOR," MiCCAi Conference, Sep. 2017, 25 pages.
Hughes-Hallett et al., "Inattention blindness in surgery," Imperial College London, 17 pages.
International Search Report and Written Opinion mailed Jun. 28, 2019, issued in corresponding International Application No. PCT/US2019/013709, filed Jan. 15, 2019, 13 pages.

* cited by examiner

STEP-BASED SYSTEM FOR PROVIDING SURGICAL INTRAOPERATIVE CUES

This application claims the benefit of U.S. Application No. 62/619,650, filed on Jan. 19, 2018, the contents of which are incorporated herein by reference.

TECHNICAL FIELD

This disclosure relates generally to surgical technologies, and in particular, relates to robot-assisted surgery.

BACKGROUND INFORMATION

Robotic or computer assisted surgery uses robotic systems to aid in surgical procedures. Robotic surgery was developed as a way to overcome limitations (e.g., spatial constraints associated with a surgeon's hands, inherent shakiness of human movements, and inconsistency in human work product, etc.) of pre-existing surgical procedures. In recent years, the field has advanced greatly to limit the size of incisions, and reduce patient recovery time.

In the case of open surgery, autonomous instruments may replace traditional tools to perform surgical motions. Feedback-controlled motions may allow for smoother surgical steps than those performed by humans. For example, using a surgical robot for a step such as rib spreading may result in less damage to the patient's tissue than if the step were performed by a surgeon's hand. Additionally, surgical robots can reduce the amount of time in the operating room by requiring fewer steps to complete a procedure.

Even when guiding surgical robots, surgeons can easily be distracted by additional information provided to them during a surgical case. Any user interface (UI) that attempts to provide all relevant information to the surgeon at once may become crowded. Overlays have been shown to distract surgeons, causing inattention blindness, and actually hinder their surgical judgment rather than enhance it.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system and method for a step-based approach to provide surgical intraoperative cues are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Surgeons often ask nurses for specific information that becomes important for them to know at specific times during a surgical case (e.g., medication the patient is under, available preoperative images). It takes time for nurses to find that information in computer systems, and it distracts the nurses from what they are doing. Sometimes the information cannot be found in a timely manner. Moreover, a main task of nurses is to predict which instrument the surgeon will need next and to have it ready when the surgeon asks for it. And sometimes the nurse may not accurately predict which instrument the surgeon needs.

In addition, surgical robots may be able to support apps, but these apps may not be easily discoverable, or surgeons may not want to interrupt what they are doing to open the right app at the right time, even if these apps might improve the surgery (similar to surgeons not using indocyanine green (ICG) to highlight critical structures because it takes time and effort).

Disclosed here is a system that recognizes which step the surgical procedure is at (temporally, spatially, or both), in real time, and provides cues to the surgeon based on the current, or an upcoming, surgical step. Surgical step recognition can be done in real time using machine learning. For example, machine learning may include using deep learning (applied frame by frame), or a combination of a convolutional neural net (CNN) and temporal sequence modeling (e.g., long short-term memory (LSTM)) for multiple spatial-temporal contexts of the current surgical step, which is then combined with the preceding classification result sequence, to enable real-time detection of the surgical step.

For example, the system can identify that the surgery is at "trocar placement" and provide a stadium view of the operation, or a schematic of where the next trocar should be placed, or provide guidance as to how a trocar should be inserted and/or which anatomical structures are expected under the skin and what the surgeon should be mindful of. Similarly, the system can identify that the surgery is about to begin tumor dissection and bring up the preoperative magnetic resonance image (MRI) or the relevant views from an anatomical atlas. The machine learning algorithm may learn from surgical workflows, or it can be taught by recorded user interactions (e.g., "surgeon A" always starts the clock app when he fires the stapler, the system can recognize when the stapler is firing from the video, and knows which surgeon is operating from preoperative planning and/or automatic detection—e.g., the user's "fingerprint" from how the user is using the system—so the system can automatically start the clock app for him/her). Similarly, in some embodiments, the system may predict the next instrument a surgeon needs, or provide a roadmap of surgical instruments needed. The system may compile this list from which instruments were needed in past surgeries.

In a different embodiment, after an initial time period, the system can estimate how long is left in the procedure. It can then provide an estimated "time of arrival" (when the procedure will be completed) as well as an "itinerary", that is the list of steps left to complete the case. This can be done using machine learning, where any full-length video can be used as training data (for each frame or video segment, the label is the time left until the end of the case). Preoperative imaging or additional data about the patient and/or the surgeon can be used in training. For example, if the first five steps went smoothly, but the tumor being excised is large, the surgery might take longer than if the first five steps were very slow (because of a lot of adhesion), but the tumor is relatively small. Patient body mass index (BMI) can also correlate with dissection time. Having an estimate of the time left during the operation can help with operating room scheduling (e.g., when will staff rotate, when will the next case will start), family communication (e.g., when is surgery likely to be complete), and even with the case itself (e.g., the anesthesiologist starts waking the patient up about 30 min before the anticipated end of the case). Like with estimated time of arrival when driving a car, the estimated time left for the case can fluctuate over the course of the procedure. The system could also send automatic updates to other systems (e.g., the operating room scheduler).

In another embodiment the same system may be used in a web portal when videos are reviewed, to enhance surgical training. For example, a stadium view or an actual 360 over-the-bed camera feed (synchronized to the endoscope feed) is provided during viewing of the surgical video, so that a student sees how the surgeon's actions translate into robot motion. Similarly, specific textbook pages can be displayed side by side with the main surgical field at specific steps of the case. In some embodiments, the students may view the surgery in the web portal sometime after the surgery.

Figure 1:
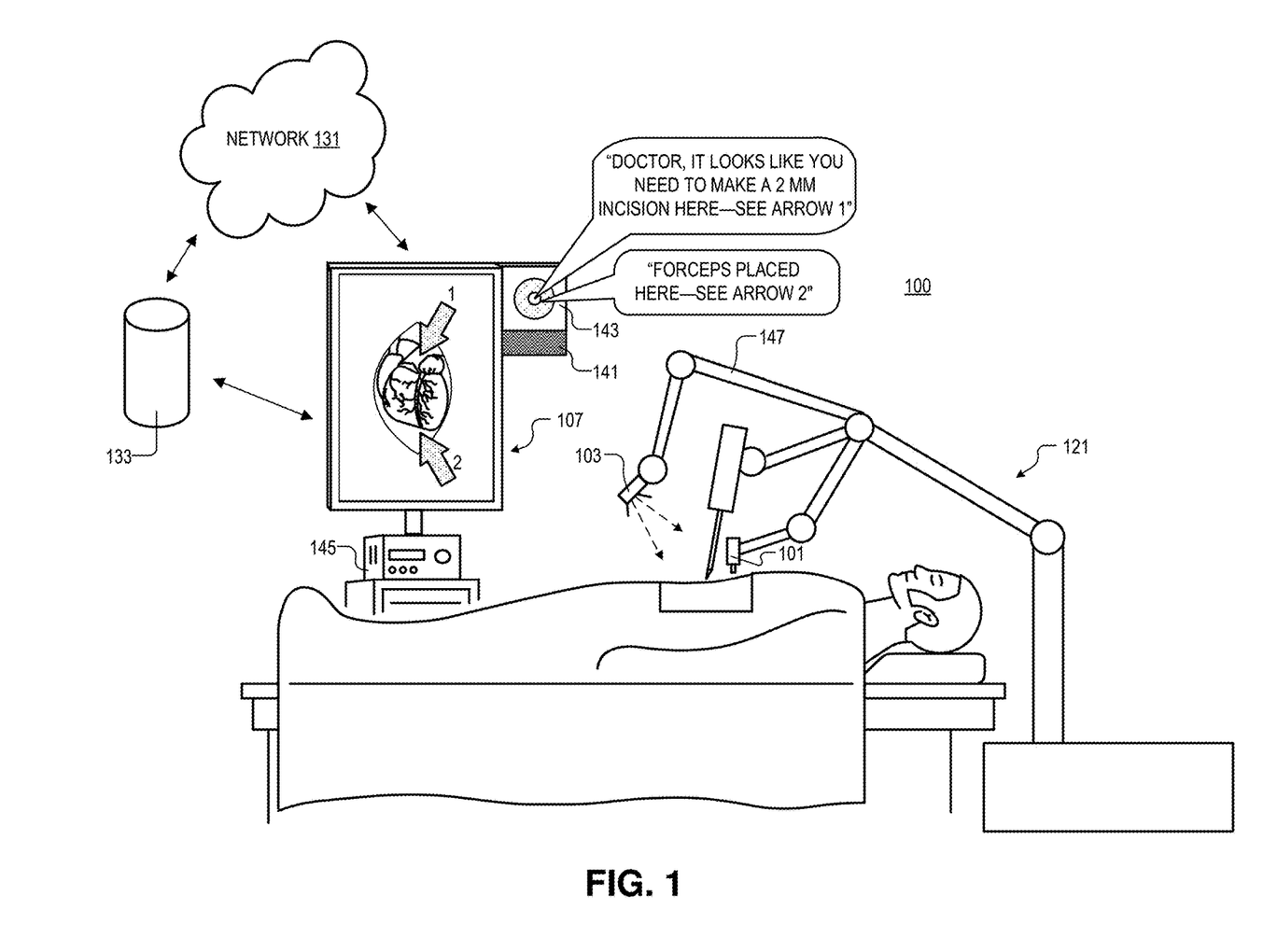
FIG. 1 illustrates a system for robot-assisted surgery, in accordance with an embodiment of the present disclosure.

FIG. 1 illustrates a system for robot-assisted surgery, in accordance with an embodiment of the present disclosure. System 100 includes surgical robot 121 (including arms 147), camera 101, light source 103, display 107, controller 145, network 131, storage 133, speaker 143, and microphone 141. All of these components may be coupled together to communicate either by wires or wirelessly.

As shown, surgical robot 121 may be used to hold surgical instruments (e.g., each arm 147 holds an instrument at the distal ends of arms 147) and perform surgery, diagnose disease, take biopsies, or conduct any other procedure a doctor could perform. Surgical instruments may include scalpels, forceps, cameras (e.g., camera 101, which may include a CMOS image sensor) or the like. While surgical robot 121 only has three arms, one skilled in the art will appreciate that surgical robot 121 is merely a cartoon illustration, and that surgical robot 121 can take any number of shapes depending on the type of surgery needed to be performed and other requirements. Surgical robot 121 may be coupled to processing apparatus 145, network 131, and/or storage 133 either by wires or wirelessly. Furthermore, surgical robot 121 may be coupled (wirelessly or by wires) to a tactile user interface (UI) to receive instructions from a surgeon or doctor (e.g., the surgeon manipulates the UI to move and control arms 147). The tactile user interface, and user of the tactile user interface, may be located very close to the surgical robot 121 and patient (e.g., in the same room) or may be located many miles apart. Thus, surgical robot 121 may be used to perform surgery where a specialist is many miles away from the patient, and instructions from the surgeon are sent over the internet or secure network (e.g., network 131). Alternatively, the surgeon may be local and may simply prefer using surgical robot 121 for example because robot 121 can better access a portion of the body than the hand of the surgeon.

As shown, an image sensor (in camera 101) is coupled to capture first images (e.g., a video stream) of a surgical procedure, and display 107 is coupled to show second images (which may include a diagram of human anatomy, a preoperative image, or an annotated version of an image included in the first images). Controller 145 is coupled to camera 101, and coupled to display 107 to output the second images. Controller 145 includes logic that when executed by controller 145 causes system 100 to perform a variety of operations. For example, controller 145 may receive the first images from the image sensor, and identify a surgical step (e.g., initial incision, grasping tumor, cutting tumor away from surrounding tissue, close wound, etc.) in the surgical procedure from the first images. In one embodiment, identification can be not just from the videos alone, but also from the rest of the data coming from the robot (e.g., instruments, telemetry, logs, etc.). The controller may then display the second images on display 107 in response to identifying the surgical step. The second images may be used to guide the doctor during the surgery. For example, system 100 may recognize that an initial incision for open heart surgery has been performed, and in response, display human anatomy of the heart for the relevant portion of the procedure. In another embodiment, system 100 may recognize that the excision of a tumor is being performed, so the system displays a preoperative image (e.g., magnetic resonance image (MM), X-ray, or computerized tomography (CT) scan, or the like) of the tumor to give the surgeon additional guidance. In yet another embodiment, display 107 could show an image included in the first images that has been annotated. For example, after recognizing the surgical step, system 100 may prompt the surgeon to complete the next step by showing the surgeon an annotated image. In the depicted embodiment, system 100 annotated the image data output from the camera 101 by adding arrows to the images that indicate where the surgeon needs to place forceps, and where the surgeon needs to make an incision. Put another way, the image data may be altered to include an arrow or other highlighting that conveys information to the surgeon. In one embodiment, the image data may be altered to include a visual representation of how confident the system is that the system is providing the correct information (e.g., a confidence interval like "75% confidence"). For example, appropriate cutting might be at a specific position (a line) or within a region of interest.

In the depicted embodiment, microphone 141 is coupled to controller 145 to send voice commands from a user to controller 145. For example, the doctor could instruct system 100 by saying "OK computer, display patient's pre-op MRI". System 100 would convert this spoken text into data, and recognize the command using natural language processing or the like. Similarly, speaker 143 is coupled to controller 145 to output audio. In the depicted example, the audio is prompting or cuing the surgeon to take a certain action "DOCTOR, IT LOOKS LIKE YOU NEED TO MAKE A 2 MM INCISION HERE—SEE ARROW 1", and "FORCEPS PLACED HERE—SEE ARROW 2". These audio commands may be output in response to system 100 identifying the specific surgical step from the first images in the video feed captured by camera 101.

In the depicted embodiment, the logic may include a machine learning algorithm trained to recognize surgical steps from the first images. The machine learning algorithm may include at least one of a convolutional neural network (CNN) or temporal sequence model (e.g., long short-term memory (LSTM) model). The machine learning algorithm may also, in some embodiments include, a deep learning algorithm, support vector machines (SVM), k-means clustering, or the like. The machine learning algorithm may identify the anatomical features by at least one of luminance, chrominance, shape, or location in the body (e.g., relative to other organs, markers, etc.). Further, controller 145 may identify anatomical features in the video using sliding window analysis. In some embodiments, controller 145 stores at least some image frames from the first images in memory (e.g., local, on network 131, or in storage 133), to recursively train the machine learning algorithm. Thus, system 100 brings a greater depth of knowledge and additional confidence to each new surgery.

It is also appreciated that the machine learning algorithm may be used to annotate the image of the surgical procedure, included in the first images, by highlighting a piece of anatomy in the image (e.g., adding an arrow to the image, circling the anatomy with a box, changing the color of the anatomy, or the like). The algorithm may also highlight the location of a surgical step (e.g., where the next step of the procedure should be performed), highlight where a surgical instrument should be placed (e.g., where the scalpel should cut, where forceps should be placed next, etc.), or automatically optimize camera placement (e.g., move the camera to the position that shows the most of the surgical area, or the like). The algorithm may also estimate a remaining duration of the surgical procedure, in response to identifying the surgical step. For example, the algorithm could see that the final suturing step is about to occur, and recognize that, on average, there are 15 minutes until completion of the surgery. This may be used to update operating room calendars in real time, or inform family in the waiting room of the remaining time. Moreover, data about the exact length of a procedure could be collected and stored in memory, along with patient characteristics (e.g., body mass index, age, etc.) to better inform how long a surgery will take for subsequent surgeries of similar patients.

In the depicted embodiment, surgical robot 121 also includes light source 103 (e.g., LEDs or bulbs) to emit light and illuminate the surgical area. As shown, light source 103 is coupled to processing apparatus 107, and processing apparatus may vary at least one of an intensity of the light emitted, a wavelength of the light emitted, or a duty ratio of the light source. In some embodiments, the light source may emit visible light, IR light, UV light, or the like. Moreover, depending on the light emitted from light source 103, camera 101 may be able to discern specific anatomical features. For example, a contrast agent that binds to tumors and fluoresces under UV light may be injected into the patent. Camera 101 could record the fluorescent portion of the image, and controller 145 may identify that portion as a tumor.

In one embodiment, image/optical sensors (e.g., camera 101), pressure sensors (stress, strain, etc.) and the like are all used to control surgical robot 121 and ensure accurate motions and applications of pressure. Furthermore, these sensors may provide information to a processor (which may be included in surgical robot 121, controller 145, or another device) which uses a feedback loop to continually adjust the location, force, etc. applied by surgical robot 121. In some embodiments, sensors in the arms of surgical robot 121 may be used to determine the position of the arms relative to organs and other anatomical features. For example, surgical robot may store and record coordinates of the instruments at the end of the arms, and these coordinates may be used in conjunction with video feed to determine the location of the arms and anatomical features. It is appreciated that there are a number of different ways (e.g., from images, mechanically, time-of-flight laser systems, etc.) to calculate distances between components in system 100 and any of these may be used to determine location, in accordance with the teachings of present disclosure.

Figure 2:
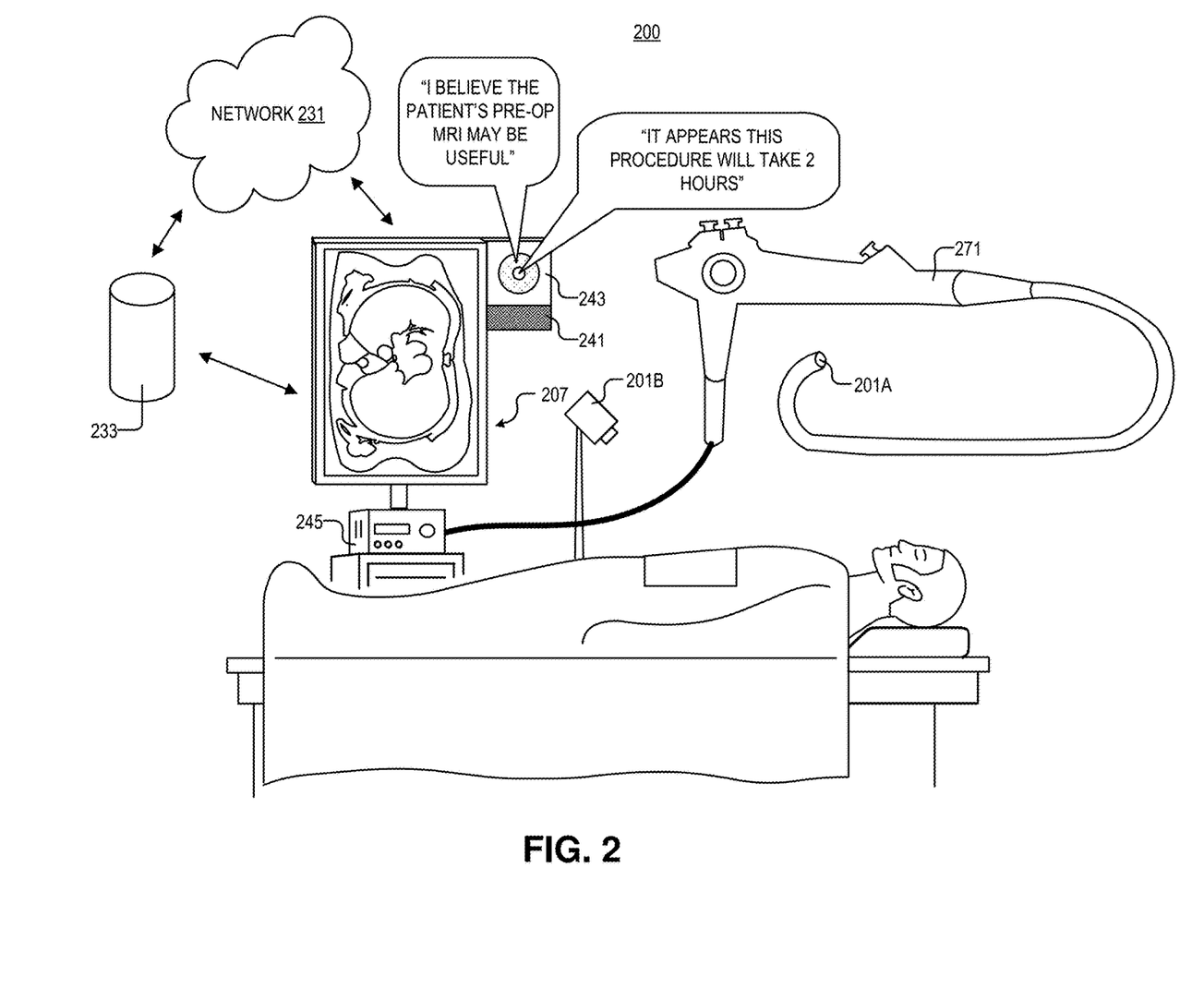
FIG. 2 illustrates another system for robot-assisted surgery, in accordance with an embodiment of the present disclosure.

FIG. 2 illustrates another system 200 for robot-assisted surgery, in accordance with an embodiment of the present disclosure. It is appreciated that system 200 includes many of the same features as system 100 of FIG. 1. Moreover, it is appreciated that systems 100 and 200 are not mutually exclusive, for instance the endoscope in system 200 may be used in conjunction with, or may be part of, the surgical robot in system 100. Systems 100 and 200 have merely been drawn separately for ease of illustration.

In addition to the components depicted in FIG. 1, FIG. 2 shows endoscope 271 (including a first camera 201A, with an image sensor, disposed in the distal end of endoscope 271), and a second camera 201B. In the depicted embodiment, endoscope 271 is coupled to controller 245. First images of the surgery may be provided by camera 201A in endoscope 271, or by second camera 201B, or both. It is appreciated that second camera 201B shows a higher-level view (viewing both the surgery and the operating room) of the surgical area than camera 201A in endoscope 271.

In the depicted embodiment, system 200 has identified (from the images captured by either camera 201A, camera 201B or both camera 201A and camera 201B) that the patients pre-op MRI may be useful for the surgery, and has subsequently brought up the MM on display 207. System 200 also informed the doctor that it would do this by outputting the audio command "I BELIEVE THE PATIENT'S PRE-OP MRI MAY BE USEFUL". Similarly, after capturing first images of the surgery, system 200 has recognized from the images that the surgery will take approximately two hours. System 200 has alerted the doctor of the ETA. In one embodiment, system 200 may have automatically updated surgical scheduling software after determining the length of the procedure. System 200 may also have announced the end time of the surgery to the waiting room or the lobby.

Figure 3:
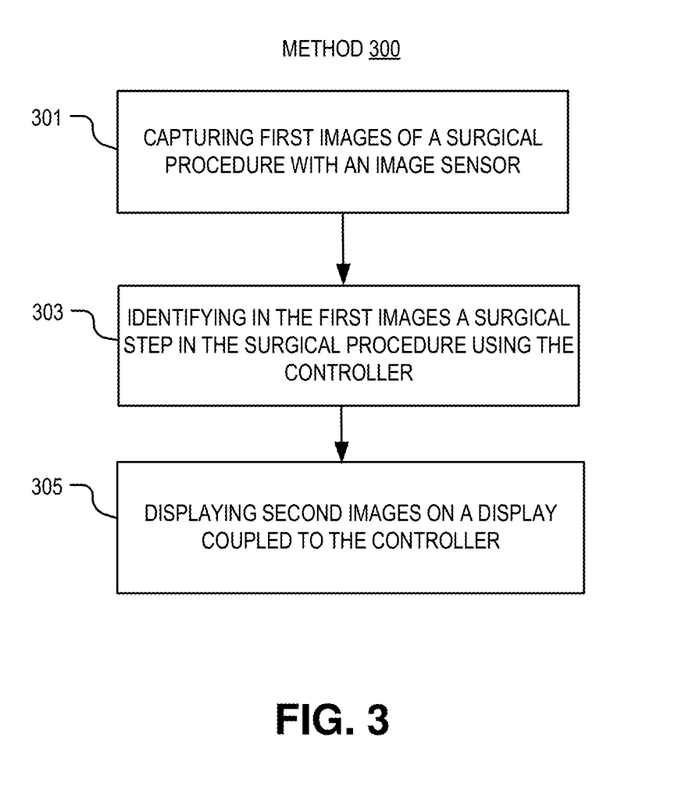
FIG. 3 illustrates a method for providing intraoperative cues, in accordance with an embodiment of the present disclosure.

FIG. 3 illustrates a method 300 for providing intraoperative cues, in accordance with an embodiment of the present disclosure. It is appreciated that numbered blocks 301-305 may occur in any order and even in parallel. Additionally, blocks may be added to, or removed from, method 300 in accordance with the teachings of the present disclosure.

Block 301 illustrates capturing first images of a surgical procedure with an image sensor. In some embodiments this includes capturing images of a birds-eye view of the surgical procedure (e.g., camera positioned above the incision), capturing images from inside the incision (e.g., with an endoscope), capturing images of the surgical room (e.g., to see which step the doctors are performing), or capturing a combination of these images. One of ordinary skill in the art having the benefit of the present disclosure will appreciate that cameras may be located anywhere in the operating room, or even outside of the operating room, to capture images for the system to process/use.

In some embodiments, the captured first images may be read out of the image sensor with readout circuitry as image data. The image data is then sent to memory, which may be local, remote, or a combination of the two.

Block 303 shows identifying a surgical step (captured in the first images) in the surgical procedure using the controller. In some embodiments, the controller includes (e.g., stored in memory) a machine learning algorithm trained to recognize surgical steps from the first images. In one embodiment, the machine learning algorithm includes at least one of a convolutional neural network (CNN), long short-term memory (LSTM), or a combination of the two. Before the surgery, the machine learning algorithm may be trained on videos of surgical procedures to recognize the different steps and the organs encountered. The machine learning algorithm may be trained iteratively, and corrected by the surgeons/nurses when errors are encountered. In some embodiments, the machine learning algorithm may be used to estimate a remaining duration of the surgical procedure, in response to identifying the surgical step. For example, the machine learning algorithm may recognize a specific suturing step, and realize that only 15 minutes remain in the surgery.

In some embodiments, the image data is accessed by the machine learning algorithm from either local or remote storage. The processor may be local (e.g., physical graphics processors, general purpose processor, or the like, which may be disposed in the robot) or may be distributed (e.g., virtual machines running on many servers). The machine learning algorithm identifies patterns in the image data to recognize the various steps in the surgical procedure.

Block 305 describes displaying second images on a display coupled to the controller in response to determining the surgical step. The second images may include at least one of a diagram of human anatomy, a preoperative image, an intraoperative image, or an image included in the first images that has been annotated by the system. In one embodiment, annotating the image included in the first images includes at least one of highlighting a piece of anatomy in the image, highlighting the location of a surgical step, or highlighting where a surgical instrument should be placed. One will appreciate that highlighting may include any image alteration technique that draws the user's attention to a specific feature or location (e.g., change the color of the feature, draw an arrow towards the feature, etc.). Highlighting could also include other feedback mechanisms (e.g., audio, haptic), or something in the room itself (e.g., the lights are turned on/off, some LED turns red, displays change what they are showing to staff, etc.).

In one embodiment, an intraoperative image may include an ultrasound. For example, in partial nephrectomy, if an intraoperative ultrasound is deemed necessary at that specific step, then the controller may be coupled to receive the ultrasound and then show the ultrasound image on the display.

In some embodiments, after recognizing the surgical step, the system may output audio commands to a user of the system from a speaker. The system may cue the user to take certain actions, show the user where the next surgical step should be, or alert the user if an action is taken that does not normally occur in a procedure (e.g., alert the doctor to a surgical tool left inside the patient). The system may make a noise, or vocalize the specific problem. In some embodiments, the system may capture voice commands with a microphone coupled to the controller, and in response to capturing the voice commands, display a preoperative image. For example, the doctor may tell the system "OK computer, show patient's chest X-ray", and the system may display the chest X-ray on the screen to aid the doctor.

In embodiments where the system annotates the first images, the controller may modify the image data to include additional features in the data output to the screen (e.g., overlaying arrows on the original image). Intelligently annotating video data as it is captured in real time, is a process that cannot be performed by a human brain. Moreover, real-time intelligent modification of surgical videos represents an improvement in the functioning of computer systems generally, and also demonstrates an improvement to the robotic or computer-assisted surgical field. In embodiments where the system recalls a preoperative image or a diagram of human anatomy, the machine learning algorithm is using the captured image data to recall a wholly different set of image data and may pour through vast tracks of image data that otherwise could not be performed by a human in real time. It is appreciated that recalled images may also be annotated (e.g., modified to draw attention to a certain feature). Thus the recalled image data may be altered (e.g., by including an arrow or a box in the image) to highlight certain features.

In some embodiments, the system could also alert the hospital that someone else should come to the rescue of the surgeon, or that someone else should take over because a new problem arose in the surgery that the surgeon does not have enough experience dealing with. Or in other examples, the hospital may be notified if an unexpected event occurs such as heart failure and a crash cart or other device is needed.

Figure 4:
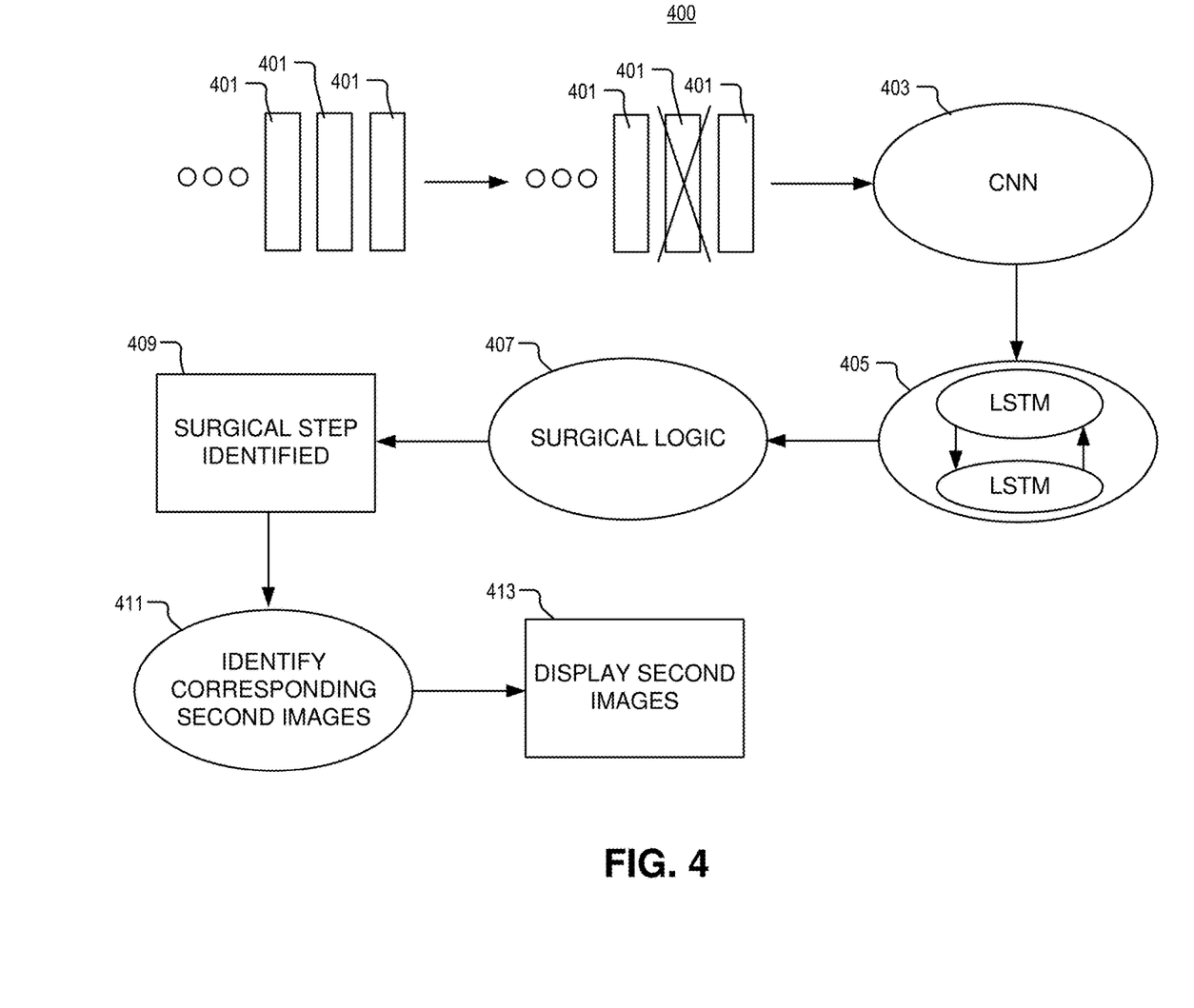
FIG. 4 depicts an architecture for identification of surgical steps, in accordance with an embodiment of the present disclosure.

FIG. 4 depicts an example architecture 400 for identification of surgical steps, in accordance with an embodiment of the present disclosure. One of skill in the art will appreciate that there may be additional, or fewer, steps and pieces of architecture, and that the components depicted may occur in different orders and even in parallel.

As shown, images 401 (e.g., frames in a video feed) may be received from an image sensor or camera with a controller or processing apparatus. In the depicted embodiment, some of these frames are removed from consideration to reduce the processing power required (see e.g., image 401 with an "X" through it). For example, one frame every second may be used to perform image recognition calculations, while other frames are excluded. This is possible because surgery generally moves at a slow, methodical pace; accordingly, to identify a surgical step in real time, the system may only need to process one frame every second, or one frame every few seconds.

The images may then be fed into a convolutional neural network (CNN) 403 (e.g., NasNet-A) which has been trained to identify surgical steps in an image, and output feature vectors (which, in one embodiment, includes a probability distribution of events taking place in the image—e.g., the probability of an incision being cut, the probability of forceps being placed in the body, or the like). CNN 403 may be trained with labeled ground-truth images. For example, surgical images may be labeled and fed to CNN 403 to train CNN 403 to identify various surgical steps by the types of surgical instruments present in the image, the organs present in the image, the location of the image relative to the human body, or the like. One of ordinary skill in the art having the benefit of the present disclosure will appreciate that convolutional neural networks may be used and trained to identify objects in images when supplied with properly labeled ground-truth image data.

In the depicted embodiment, the feature vectors for the images 403 received by the CNN 403 are output to a recurrent neural network (here, a layered long-short term memory (LSTM) network 405 with self-attention and/or positional encoding). While CNN 403 may be used to identify features in images, LSTM 405 may be used to identify temporal patterns in the vectors (e.g., how the feature vectors change over time) output from CNN 403 to further identify a surgical step. For example, LSTM 405 may be able to confidently identify a surgical step from the presence of a particular surgical instrument (e.g., identified in the images using CNN 403) for a number of frames, and output its own feature vectors including the probabilities that various events are occurring in a set of frames. In some embodiments, the information output from CNN 403 may be less reliable to identify surgical steps than using both CNN 403 and LSTM 405 in series. This is because the image sensor may shake or become temporarily blocked during surgery, thus resulting in a low quality image and subsequently a poor assessment of the surgical step or surgical features in the image by CNN 403 for a single frame. However, if the poor assessment is output to LSTM 405, the system my still identify the correct surgical step because LSTM 405 takes into consideration other images that have previously been correctly identified by CNN 403. Put another way, a single frame may not be sufficient to determine the precise surgical step. In some embodiments, it may be necessary to take into account the historical context (e.g., a short sequence or a longer sequence of video frames) to determine the action actually being performed on the anatomy.

In the depicted embodiment, the vector output from LSTM 405 may be received with surgical logic 407. Surgical logic 407 may be a final check that the machine learning algorithms 403/405 are outputting vectors that make intuitive sense based on the known progression of a particular surgery. For example, if the output of the machine learning algorithms indicates that the most probable current surgical step is "suturing to close an incision" but no incision has been made yet, the surgical logic may flag this as an error, or output the second most probable event (e.g., "preparing surgical area for incision") if the second most probable event makes sense in the context of the surgery. After being checked with surgical logic 407 a surgical step may be positively identified by the system (e.g., block 409).

The identified surgical step 409 may then be used to recall (second) image data (e.g., block 411) or other data to a display to aid the surgeon. For example, the system may be programmed to call the preoperative imaging (e.g., an MRI) stored in a file on the system, in response to the surgeon making an incision. In some embodiments, the system my use machine learning techniques like the ones described above to "learn" the information that the surgeon wants at each step of the operation. However, in other embodiments an assistant or the like can, before surgery, simply "tie" an image to each surgical step so that once the system detects a particular step is occurring the preselected image is displayed (e.g., block 413).

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise. It is appreciated that terms like "a surgical robot" or "robot-assisted surgery" may include any system that aids or assists in surgery (e.g., a virtual assistant), and does not actually have to perform the surgery or have moving parts.

A tangible machine-readable storage medium includes any mechanism that provides (i.e., stores) information in a non-transitory form accessible by a machine or controller (e.g., a computer, network device, personal digital assistant, manufacturing tool, any device with a set of one or more processors, general-purpose processor configured by firmware/software, programmable gate array, or application specific integrated circuit, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A system for surgery, comprising:
 a controller including logic that when executed by the controller causes the system to perform operations, including:
  receiving first images of a surgical procedure;
  analyzing the first images with the controller executing a machine learning model to identify one or more surgical steps in the surgical procedure, wherein an architecture of the machine learning model includes a convolutional neural network (CNN) directed to identifying the one or more surgical steps and a recurrent neural network (RNN) directed to identifying the one or more surgical steps, wherein the CNN is coupled to RNN, and wherein the analyzing the first images includes:
   generating first feature vectors output by the CNN in response to inputting the first images into the CNN, wherein the first feature vectors include a first probability distribution that the one or more surgical steps are occurring within the first images;
   generating second feature vectors output by the RNN in response to inputting the first feature vectors output by the CNN into the RNN, wherein the second feature vectors include a second probability distribution that the one or more surgical steps are occurring within the first images; and
   identifying a surgical step included in the one or more surgical steps occurring during the surgical procedure based on the second probability distribution; and
  selecting second images related to the surgical step for display in response to the identifying the surgical step, wherein the second images include at least one of a diagram of human anatomy relevant to the surgical step, a preoperative image relevant to the surgical step, an intraoperative image relevant to the surgical step, or an annotated image of one of the first images.

2. The system of claim 1, further comprising:
a plurality of arms coupled to the controller and configured to hold surgical instruments; and
a tactile user interface coupled to the controller, wherein the controller further includes logic that when executed by the controller causes the system to perform operations, including:
in response to receiving user input from the tactile user interface, manipulating the plurality of arms.

3. The system of claim 1, further comprising:
a microphone coupled to the controller to send voice commands from a user to the controller; and
a speaker coupled to the controller to output audio.

4. The system of claim 3, wherein the controller further includes logic that when executed by the controller causes the system to perform operations, including: in response to identifying the surgical step, outputting audio commands to the user of the system from the speaker.

5. The system of claim 1, further comprising annotating the one of the first images to form the annotated image by at least one of highlighting a piece of anatomy, highlighting a location of a surgical step, or highlighting where a surgical instrument should be placed.

6. The system of claim 1, wherein the preoperative image includes a magnetic resonance image, computerized tomography scan, or an X-ray.

7. The system of claim 1, wherein the controller further includes logic that when executed by the controller causes the system to perform operations, including:
estimating a remaining duration of the surgical procedure, in response to identifying the surgical step.

8. The system of claim 1, further comprising an image sensor to capture the first images, and wherein the image sensor is disposed in an endoscope and the endoscope is coupled to the controller.

9. The system of claim 1, wherein adjacent frames included in a sequence of video frames are temporally segmented from one another by one second or longer.

10. The system of claim 1, wherein the surgical step initially identified corresponds to a most probable current surgical step associated with the first images selected from the second probability distribution, wherein the controller further includes logic that when executed by the controller causes the system to perform operations, including:
comparing the most probable current surgical step to a known progression of the surgical procedure to perform a context check; and
flagging the most probable current surgical step included in the second probability distribution as an error and selecting a second most probable current surgical step from the second probability distribution as the surgical step occurring in the surgical procedure responsive to the context check.

11. A method for operating a surgical system, comprising:
receiving first images of a surgical procedure;
analyzing the first images using a machine learning model to identify one or more surgical steps in the surgical procedure, wherein an architecture of the machine learning model includes a convolutional neural network (CNN) directed to identifying the one or more surgical steps and a recurrent neural network directed to identifying the one or more surgical steps, wherein the CNN is coupled to the RNN, and wherein the analyzing the first images includes:
generating first feature vectors output by the CNN in response to inputting the first images into the CNN, wherein the first feature vectors includes a first probability distribution that the one or more surgical steps are occurring within the first images;
generating second feature vectors output by the RNN in response to inputting the first feature vectors output by the CNN into the RNN, wherein the second feature vectors include a second probability distribution that the one or more surgical steps are occurring within the first images; and
identifying a surgical step included in the one or more surgical steps occurring during the surgical procedure based on the second probability distribution; and
selecting second images related to the surgical step for display in response to the identifying the surgical step, wherein the second images include at least one of a diagram of human anatomy relevant to the surgical step, a preoperative image relevant to the surgical step, an intraoperative image relevant to the surgical step, or an annotated image of one of the first images.

12. The method of claim 11, further comprising estimating a remaining duration of the surgical procedure using the machine learning architecture, in response to the identifying the surgical step.

13. The method of claim 12, further comprising:
automatically informing, by the controller, an operating room scheduler when an estimation of the remaining duration by the machine learning architecture changes.

14. The method of claim 11, further comprising outputting audio commands from a speaker coupled to the controller, in response to determining the surgical step.

15. The method of claim 14, further comprising outputting a duration of the surgical procedure from the speaker.

16. The method of claim 11, further comprising annotating the one of the first images to form the annotated image by at least one of highlighting a piece of anatomy, highlighting the location of a surgical step, or highlighting where a surgical instrument should be placed.

17. The method of claim 11, wherein the preoperative image includes a magnetic resonance image, computerized tomography scan, or an X-ray.

18. The method of claim 11, wherein the recurrent neural network comprises a long short-term memory (LSTM) network.

19. The method of claim 11, wherein the first images are captured with an image sensor disposed in an endoscope and the endoscope is coupled to the controller.

20. The method of claim 11, further comprising:
capturing voice commands with a microphone coupled to the controller; and
in response to capturing the voice commands, displaying the preoperative image.

21. The method of claim 11, further comprising, in response to determining the surgical step, starting a timer.

22. The method of claim 11, further comprising:
removing, from consideration of the machine learning model, one or more images included in the first images of the surgical procedure captured by the image sensor to reduce required processing power.

23. At least one non-transitory machine-accessible storage medium that provides instructions that, when executed by a machine, will cause the machine to perform operations, comprising:
receiving first images of a surgical procedure;

analyzing the first images using a machine learning model to identify one or more surgical steps in the surgical procedure wherein an architecture of the machine learning model includes a convolutional neural network (CNN) directed to identifying the one or more surgical steps and a recurrent neural network (RNN) directed to identifying the one or more surgical steps, wherein the CNN is coupled to the RNN, and wherein the analyzing the first images includes:
generating first feature vectors output by the CNN in response to inputting the first images into the CNN, wherein the first feature vectors include a first probability distribution that the one or more surgical steps are occurring within the first images;
generating second feature vectors output by the RNN in response to inputting the first feature vectors output by the CNN into the RNN, wherein the second feature vectors include a second probability distribution that the one or more surgical steps are occurring within the first images; and
identifying a surgical step included in the one or more surgical steps occurring during the surgical procedure based on the second probability distribution; and
in response to identifying the surgical step, estimating a remaining duration of the surgical procedure to provide a real time update of when a completion of the surgical procedure is expected to occur during the surgical procedure.

24. At least one non-transitory machine-accessible storage medium that provides instructions that, when executed by a machine, will cause the machine to perform operations, comprising:

receiving first images of a surgical procedure;
analyzing the first images using a machine learning model to identify one or more surgical steps in the surgical procedure, wherein an architecture of the machine learning model includes a convolutional neural network (CNN) directed to identifying the one or more surgical steps and a recurrent neural network (RNN) directed to identifying the one or more surgical steps, wherein the CNN is coupled to the RNN, and wherein the analyzing the first images includes:
generating first feature vectors output by the CNN in response to inputting the first images into the CNN, wherein the first feature vectors include a first probability distribution that the one or more surgical steps are occurring within the first images;
generating second feature vectors output by the RNN in response to inputting the first feature vectors output by the CNN into the RNN, wherein the second feature vectors include a second probability distribution that the one or more surgical steps are occurring within the first images; and
identifying a surgical step included in the one or more surgical steps occurring during the surgical procedure based on the second probability distribution; and
selecting second images related to the surgical step for display, wherein the second images include at least one of a diagram of human anatomy relevant to the surgical step, a preoperative image relevant to the surgical step, an intraoperative image relevant to the surgical step, or an annotated image of one of the first images.

* * * * *